United States Patent
Liao et al.

(10) Patent No.: US 10,611,711 B1
(45) Date of Patent: Apr. 7, 2020

(54) METHOD FOR PREPARING 1,4-CYCLOHEXANEDIMETHANOL

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Sung-Chieh Chao, Taipei (TW); Chia-Ruey Tsai, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 16/575,584

(22) Filed: Sep. 19, 2019

(30) Foreign Application Priority Data

Apr. 15, 2019 (TW) .................. 108113092

(51) Int. Cl.
| | | |
|---|---|---|
| *C07C 29/17* | (2006.01) | |
| *C07C 31/27* | (2006.01) | |
| *B01J 23/86* | (2006.01) | |
| *C07C 29/149* | (2006.01) | |
| *C07C 69/75* | (2006.01) | |
| *C07C 67/303* | (2006.01) | |
| *B01J 23/46* | (2006.01) | |

(52) U.S. Cl.
CPC .......... *C07C 29/177* (2013.01); *B01J 23/462* (2013.01); *B01J 23/868* (2013.01); *C07C 29/149* (2013.01); *C07C 31/276* (2013.01); *C07C 67/303* (2013.01); *C07C 69/75* (2013.01)

(58) Field of Classification Search
CPC ... C07C 29/149; C07C 67/303; C07C 31/276; C07C 69/75; C07C 2601/14; B01J 23/868; B01J 23/462
See application file for complete search history.

(56) References Cited

U.S. PATENT DOCUMENTS 6,187,968 B1 * 2/2001 Itoh ...................... C07C 29/149
568/831

\* cited by examiner

*Primary Examiner* — Jafar F Parsa
(74) *Attorney, Agent, or Firm* — Li & Cai Intellectual Property (USA) Office

(57) ABSTRACT

A method for preparing 1,4-cyclohexanedimethanol is provided. The method allows hydrogen gas fed into a reaction tank to be uniformly dispersed in a reaction solution by a gas-introducing mixer having air-extracting, air-exhausting and mixing functions. Accordingly, the reaction solution has a high concentration of dissolved hydrogen gas so that the reaction time of hydrogenation can be reduced to as short as possible. Furthermore, the method uses a hydrogenation catalyst having many advantages such as high activity and low cost. The added amount of the hydrogenation catalyst can be reduced under the operation of the gas-introducing mixer.

8 Claims, 3 Drawing Sheets

METHOD FOR PREPARING 1,4-CYCLOHEXANEDIMETHANOL

CROSS-REFERENCE TO RELATED PATENT APPLICATION

This application claims the benefit of priority to Taiwan Patent Application No. 108,113,092, filed on Apr. 15, 2019. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a method for preparing 1,4-cyclohexanedimethanol, and more particularly to a hydrogenation reaction-based method for preparing 1,4-cyclohexanedimethanol.

BACKGROUND OF THE DISCLOSURE 1,4-cyclohexanedimethanol is an alicyclic diol having a symmetric structure. A resin synthesized by 1,4-cyclohexanedimethanol has good chemical stability, transparency and stiffness. The production of 1,4-cyclohexanedimethanol is generally implemented by the hydrogenation method.

As shown in FIG. 1, a conventional hydrogenation tank 10 for producing 1,4-cyclohexanedimethanol is provided with an impeller mixer 20. The impeller mixer 20 can use a blade 22 disposed at a terminal end of a rotating shaft 21 to mix a reaction solution 30. One end of a hydrogen gas tube is immersed in the reaction solution 30 for directing and forcing hydrogen gas to contact the reaction solution 30. Accordingly, the reaction solution 30 can be hydrogenated in the presence of hydrogen gas and a catalyst so as to obtain 1,4-cyclohexanedimethanol. However, the conventional hydrogenation tank 10 may have a low yield of 1,4-cyclohexanedimethanol due to a low contact efficiency of hydrogen gas and the reaction solution 30 in the hydrogenation reaction.

SUMMARY OF THE DISCLOSURE

In response to the above-referenced technical requirements, the present disclosure provides a method for preparing 1,4-cyclohexanedimethanol, which has a yield of 1,4-cyclohexanedimethanol up to 72.7-76.6%.

In one aspect, the present disclosure provides a method for preparing 1,4-cyclohexanedimethanol, including: step (a), providing a hydrogenating reaction tank equipped with a gas-introducing mixer having air-extracting, air-exhausting and mixing functions, wherein the gas-directing mixer includes a hollow rotating shaft and a blade disposed at a terminal end of the hollow rotating shaft, and the hollow rotating shaft has an air inlet hole and an air outlet hole; step (b) placing a reaction solution into the hydrogenating reaction tank, wherein the reaction solution includes cyclohexane-1,4-dicarboxylic acid diisooctyl ester and a solvent; step (c) adding a hydrogenation catalyst to the reaction solution, the hydrogenation catalyst added in an amount of 0.2-15 wt % of the amount of cyclohexane-1,4-dicarboxylic acid diisooctyl ester; step (d) feeding hydrogen gas into the hydrogenating reaction tank to maintain a hydrogen gas pressure at 20-200 bar; step (e) starting the gas-introducing mixer to bring the hollow rotating shaft to a predetermined rotation speed so as to drive the blade to mix the reaction liquid, wherein hydrogen gas above a liquid surface of the reaction solution is introduced into the hollow rotating shaft via the air inlet hole and subsequently delivered to the reaction solution via the air outlet hole, and hydrogen gas in the reaction solution is uniformly dispersed after the reaction solution is mixed by the blade; step (f) carrying out a hydrogenation reaction at 120-260° C. for 1-40 hours to hydrogenate cyclohexane-1,4-dicarboxylic acid diisooctyl ester in the reaction solution into 1,4-cyclohexanedimethanol; and step (g) cooling the reaction solution to room temperature and removing the hydrogenation catalyst and the solvent.

One of the advantages of the present disclosure is that the method for preparing 1,4-cyclohexanedimethanol of the present disclosure, which uses the hydrogenating reaction tank equipped with the gas-introducing mixer having air-extracting, air-exhausting and mixing functions, can achieve the effects as follows. First, the contact efficiency of hydrogen gas and the reaction solution can be increased. Second, the reaction solution of the hydrogenation reaction has a high concentration of dissolved hydrogen gas so that the hydrogenation catalyst has an extremely high activity and can result in a fast hydrogenation rate. Third, the hydrogenation reaction can obtain a high yield of 1,4-cyclohexanedimethanol and thus has high economic benefits.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
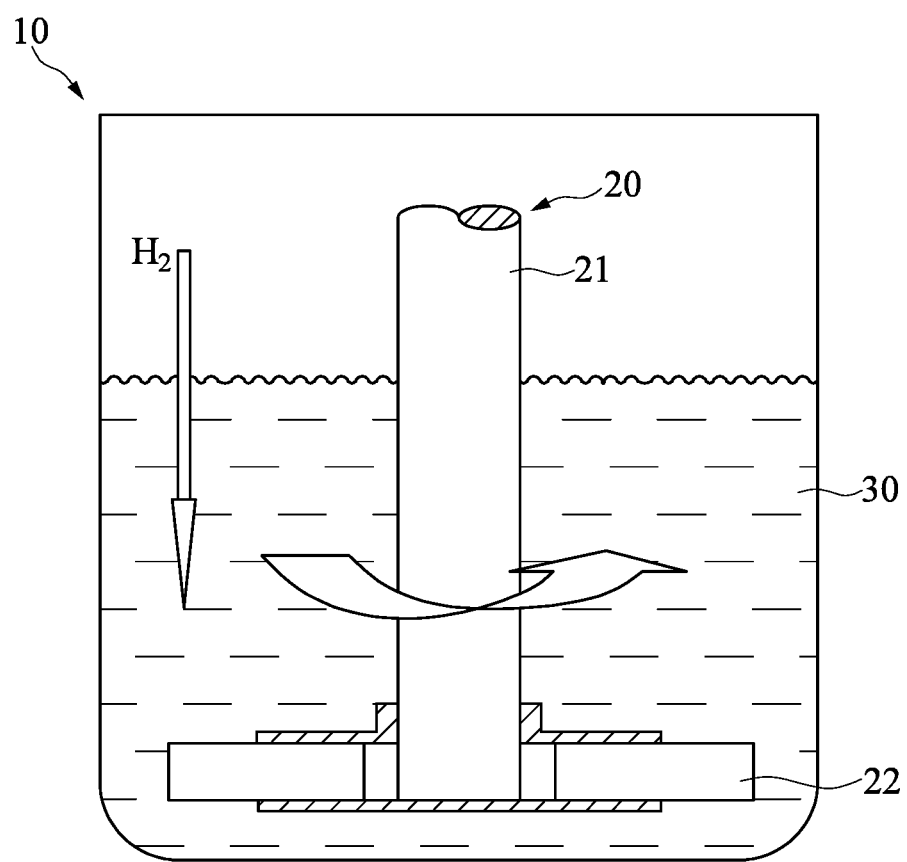
FIG. 1 is a schematic view of a conventional hydrogenation tank.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
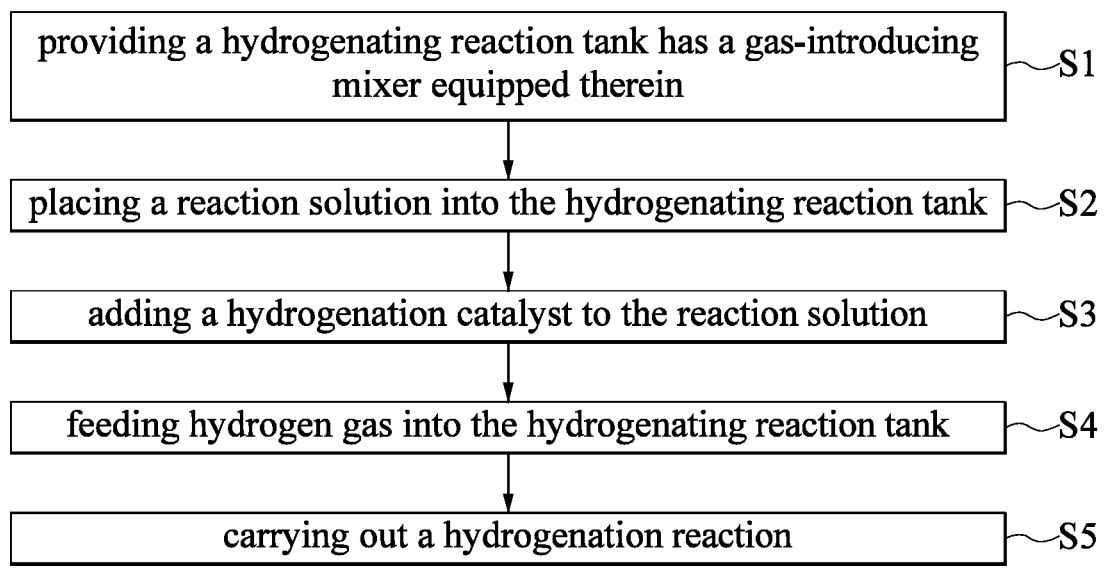
FIG. 2 is a flow chart of a method for preparing 1,4-cyclohexanedimethanol of the present disclosure.

Referring to FIG. 2, the present disclosure provides a method for preparing 1,4-cyclohexanedimethanol, which uses hydrogenate cyclohexane-1,4-dicarboxylic acid diisooctyl ester to prepare 1,4-cyclohexanedimethanol. The method mainly includes: step S1, providing a hydrogenating reaction tank that has a gas-introducing mixer equipped therein; step S2, placing a reaction solution into the hydrogenating reaction tank; step S3, adding a hydrogenation catalyst to the reaction solution; step S4, feeding hydrogen gas into the hydrogenating reaction tank; and step S5, carrying out a hydrogenation reaction.

Figure 3:
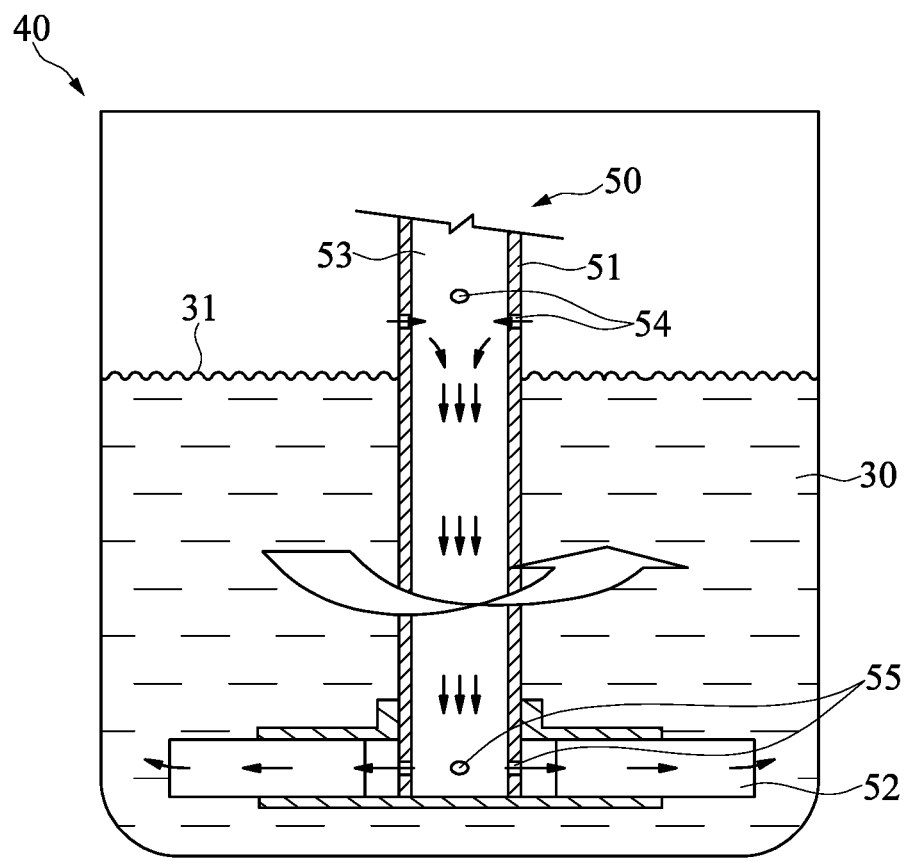
FIG. 3 is a schematic view of a hydrogenating reaction tank of the present disclosure.

Reference is made to FIG. 3, the hydrogenating reaction tank 40 provided in the step Si is used to hydrogenate cyclohexane-1,4-dicarboxylic acid diisooctyl ester so as to form 1,4-cyclohexanedimethanol. The hydrogenating reaction tank 40 has a gas-introducing mixer 50 equipped therein. The gas-introducing mixer 50 has air-extracting, air-exhausting and mixing functions, such that the contact efficiency of hydrogen gas and the reaction solution can be increased to obtain a higher yield of 1,4-cyclohexanedimethanol.

More specifically, the hydrogenating reaction tank 40 is a cylindrical pressure-resistant vessel, the height to diameter ratio of which is preferably from 0.4 to 3. In addition to the gas-introducing mixer 50, the hydrogenating reaction tank 40 can additionally have a board-type heat exchanger or a coil pipe (not shown) equipped therein for immediately removing heat released from the hydrogenation reaction to avoid heat accumulation.

The gas-introducing mixer 50 includes a hollow rotating shaft 51 and a blade 52 disposed at a terminal end of the hollow rotating shaft 51. The hollow rotating shaft 51 has a gas channel 53 therein for delivering hydrogen gas. The hollow rotating shaft 51 has an upper part provided with a number of air inlet holes 54 in communication with the gas channel 53. In use, the air inlet holes 54 are located above a liquid surface 31 of the reaction solution 30 containing cyclohexane-1,4-dicarboxylic acid diisooctyl ester, such that hydrogen gas can be introduced into the gas channel 53. The hollow rotating shaft 51 has a lower part provided with a number of air outlet holes 55 in communication with the gas channel 53 for exhausting the introduced hydrogen gas from the gas channel 53. The blade of the gas-introducing mixer 50 can be a flat blade, a curved blade or a concave blade.

In the step S2, the reaction solution 30 can be poured into the hydrogenating reaction tank 40. The reaction solution 30 includes cyclohexane-1,4-dicarboxylic acid diisooctyl ester and a solvent. The solvent is used to dilute cyclohexane-1,4-dicarboxylic acid diisooctyl ester. The solvent may be methanol, ethanol, isopropanol, isooctanol or isodecyl alcohol, but is not limited thereto. The aforesaid solvents do not reduce the activity of the hydrogenation catalyst, and do not react with cyclohexane-1,4-dicarboxylic acid diisooctyl ester to produce unwanted by-products. When the solvent for dilution is added in an amount 1 to 3 times the amount of cyclohexane-1,4-dicarboxylic acid diisooctyl ester, the hydrogenation speed can be increased.

In the step S3, the hydrogenation catalyst is used to promote the hydrogenation of cyclohexane-1,4-dicarboxylic acid diisooctyl ester. The hydrogenation catalyst is a heterogeneous catalyst, which can be a ruthenium catalyst, a palladium catalyst, a copper catalyst, a ruthenium catalyst, a nickel catalyst or any combination thereof. In consideration of the hydrogenation rate and cost, the hydrogenation catalyst can be added in an amount of 0.2-15 wt % of the amount of cyclohexane-1,4-dicarboxylic acid diisooctyl ester, and preferably 0.5-10 wt % of the amount of cyclohexane-1,4-dicarboxylic acid diisooctyl ester.

In the step S4, the hydrogenating reaction tank 40 fed with hydrogen gas has a hydrogen gas pressure of 20-200 bar, and preferably 50-150 bar. In the step S5, the hollow rotating shaft 51 of the gas-introducing mixer 50 can reach a predetermined rotation speed so as to drive the blade 51 to mix the reaction solution 30. The predetermined rotation speed can be 1200-1500 rpm, preferably 1400 rpm. Accordingly, hydrogen gas above the liquid surface 31 of the reaction solution 30 would be extracted and introduced into the gas channel 53 via the air inlet holes 54, and subsequently discharged to the reaction solution 30 via the air outlet holes 55. The discharged hydrogen gas can be uniformly dispersed in the reaction solution 30 under the mixing action of the blade 52. Therefore, the contact efficiency of hydrogen gas and the reaction solution 30 can be increased and the reaction solution 30 can have a high concentration of dissolved hydrogen gas, so that the hydrogenation catalyst has an extremely high activity and can result in a fast hydrogenation rate.

In the step S6, the reaction temperature of the hydrogenation reaction can be 120-260° C., preferably 150-240° C., and the reaction time can be 1-40 hours, so as to hydrogenate cyclohexane-1,4-dicarboxylic acid diisooctyl ester in the reaction solution 30 into 1,4-cyclohexanedimethanol. It is worth mentioning that the hydrogenating reaction tank 40, which has the gas-introducing mixer 50 and the board-type heat exchanger or coil pipe equipped therein, can have an increased yield of 1,4-cyclohexanedimethanol. The reason is that, in the hydrogenating reaction tank 40, the contact efficiency of hydrogen gas and the reaction solution 30 can be increased, and heat generated from the hydrogenation reaction to avoid heat accumulation can be immediately removed.

After completion of the hydrogenation reaction, the reaction solution 30 is cooled to room temperature and the hydrogenation catalyst and the solvent are removed by filtration, so as to obtain a recovered product. The recovered product includes 25-50 wt % of 1,4-cyclohexanedimethanol, 50-75 wt % of the solvent, and a small amount of impurities, wherein the yield of 1,4-cyclohexanedimethanol can reach 72.7-76.6%.

Examples 1-5 and Comparative Examples 1-4 are used to more specifically illustrate the present disclosure, and serve only as exemplifications of the present disclosure without limiting the scope of the present disclosure.

Example 1

20 g of cyclohexane-1,4-dicarboxylic acid diisooctyl ester was dissolved in 20 g of isooctyl alcohol, and a reaction solution thus obtained was placed into a 1-L pressure-resistant reaction tank equipped with a gas-introducing mixer. After that, 1.6 g of a copper catalyst was added to the reaction solution and hydrogen gas was fed into the reaction tank to maintain a hydrogen gas pressure at 100 bar. Next, the gas-introducing mixer of the reaction tank was started and the reaction temperature was raised to 230° C. for carrying out a hydrogenation reaction for 30 hours. After completion of the hydrogenation reaction, the reaction solution was cooled to room temperature and the copper catalyst and isooctyl alcohol were removed by filtration, so as to obtain a reaction product for composition analysis. The results are shown in Table 1, and the yield of 1,4-cyclohexanedimethanol is 76.6%.

Example 2

The preparation method is the same as that used in Example 1. All conditions were the same as those in Example 1, except that the reaction temperature was changed to 210° C. The results are shown in Table 1, and the yield of 1,4-cyclohexanedimethanol is 72.7%.

Example 3

The preparation method is the same as that used in Example 1. All conditions were the same as in Example 1, except that the reaction temperature was changed to 240° C. The results were shown in Table 1, and the yield of 1,4-cyclohexanedimethanol is 73.7%.

Example 4

The preparation method is the same as that used in Example 1. All conditions were the same as in Example 1, except that the hydrogen gas pressure in the reaction tank was changed to 70 bar. The results were shown in Table 1, and the yield of 1,4-cyclohexanedimethanol is 52.3%.

Example 5

The preparation method is the same as that used in Example 1. All conditions were the same as in Example 1, except that the hydrogen gas pressure in the reaction tank was changed to 60 bar. The results were shown in Table 1, and the yield of 1,4-cyclohexanedimethanol is 41.5%.

Comparative Example 1

An impeller mixer was used in place of the gas-introducing mixer of the reaction tank, while other conditions were the same as those in Example 1. The results were shown in Table 1, and the yield of 1,4-cyclohexanedimethanol is 55.2%.

Comparative Example 2

The reaction temperature was changed to 210° C., while other conditions were the same as in Comparative Example 1. The results were shown in Table 1, and the yield of 1,4-cyclohexanedimethanol is 48.1%.

Comparative Example 3

The reaction temperature was changed to 240° C., while other conditions were the same as in Comparative Example 1. The results were shown in Table 1, and the yield of 1,4-cyclohexanedimethanol is 53.9%.

Comparative Example 4

The hydrogen gas pressure in the reaction tank was changed to 70 bar, while other conditions were the same as in Comparative Example 1. The results were shown in Table 1, and the yield of 1,4-cyclohexanedimethanol is 37.3%.

TABLE 1

| | Example | | | | | Comparative Example | | | |
| --- | --- | --- | --- | --- | --- | --- | --- | --- | --- |
| | 1 | 2 | 3 | 4 | 5 | 1 | 2 | 3 | 4 |
| Hydrogenating reaction tank | Equipped with gas-introducing mixer | | | | | Equipped with impeller mixer | | | |
| Cyclohexane-1,4-dicarboxylic acid diisooctyl ester (g) | 20 | 20 | 20 | 20 | 20 | 20 | 20 | 20 | 20 |
| Isooctyl alcohol (g) | 20 | 20 | 20 | 20 | 20 | 20 | 20 | 20 | 20 |
| Copper catalyst (g) | 1.6 | 1.6 | 1.6 | 1.6 | 1.6 | 1.6 | 1.6 | 1.6 | 1.6 |
| Hydrogen gas pressure (bar) | 100 | 100 | 100 | 70 | 60 | 100 | 100 | 100 | 70 |
| Reaction temperature (° C.) | 230 | 210 | 240 | 230 | 230 | 230 | 210 | 240 | 230 |
| Reaction time (Hr) | 30 | 30 | 30 | 30 | 30 | 30 | 30 | 30 | 30 |
| 1,4-cyclohexane-dimethanol (%) | 76.6 | 72.7 | 73.7 | 52.3 | 41.5 | 55.2 | 48.1 | 53.9 | 37.3 |

One of the advantages of the present disclosure is that the method for preparing 1,4-cyclohexanedimethanol of the present disclosure, which uses the hydrogenating reaction tank equipped with the gas-introducing mixer having air-extracting, air-exhausting and mixing functions, can achieve the effects as follows. First, the contact efficiency of hydrogen gas and the reaction solution can be increased. Second, the reaction solution of the hydrogenation reaction has a high concentration of dissolved hydrogen gas so that the hydrogenation catalyst has an extremely high activity and can result in a fast hydrogenation rate. Third, the hydrogenation reaction can obtain a high yield of 1,4-cyclohexanedimethanol and thus has high economic benefits.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for preparing 1,4-cyclohexanedimethanol, comprising:
    (a) providing a hydrogenating reaction tank equipped with a gas-introducing mixer having air-extracting, air-exhausting and mixing functions, wherein the gas-directing mixer includes a hollow rotating shaft and a blade disposed at a terminal end of the hollow rotating shaft, and the hollow rotating shaft has an air inlet hole and an air outlet hole;
    (b) placing a reaction solution into the hydrogenating reaction tank, wherein the reaction solution includes cyclohexane-1,4-dicarboxylic acid diisooctyl ester and a solvent;
    (c) adding a hydrogenation catalyst to the reaction solution, the hydrogenation catalyst added in an amount of 0.2-15 wt % of the amount of cyclohexane-1,4-dicarboxylic acid diisooctyl ester;
    (d) feeding hydrogen gas into the hydrogenating reaction tank to maintain a hydrogen gas pressure at 20-200 bar;
    (e) starting the gas-introducing mixer to bring the hollow rotating shaft to a predetermined rotation speed so as to drive the blade to mix the reaction liquid, wherein hydrogen gas above a liquid surface of the reaction solution is introduced into the hollow rotating shaft via the air inlet hole and subsequently delivered to the reaction solution via the air outlet hole, and hydrogen gas in the reaction solution is uniformly dispersed while the reaction solution is mixed by the blade;
    (f) carrying out a hydrogenation reaction at 120-260° C. for 1-40 hours to hydrogenate cyclohexane-1,4-dicarboxylic acid diisooctyl ester in the reaction solution into 1,4-cyclohexanedimethanol; and
    (g) cooling the reaction solution to room temperature and removing the hydrogenation catalyst and the solvent.

2. The method according to claim 1, wherein the solvent is methanol, ethanol, isopropanol, isooctanol or isodecyl alcohol.

3. The method according to claim 1, wherein in the step (c), the added amount of the hydrogenation catalyst is 0.5-10 wt % of the amount of cyclohexane-1,4-dicarboxylic acid diisooctyl ester.

4. The method according to claim 1, wherein the hydrogenation catalyst is a ruthenium catalyst, a palladium catalyst, a copper catalyst, a nickel catalyst or any combination thereof.

5. The method according to claim 1, wherein in the step (d), the hydrogen gas pressure in the hydrogenating reaction tank is maintained at 50-150 bar.

6. The method according to claim 1, wherein in the step (e), the predetermined rotation speed of the hollow rotating shaft is 1200-1500 rpm.

7. The method according to claim 1, wherein in the step (f), the hydrogenation reaction is carried out at 150-240° C.

8. The method according to claim 1, wherein the hydrogenating reaction tank has a board-type heat exchanger or a coil pipe.

* * * * *